(12) United States Patent
Hacker

(10) Patent No.: US 6,334,068 B1
(45) Date of Patent: Dec. 25, 2001

(54) INTRAOPERATIVE NEUROELECTROPHYSIOLOGICAL MONITOR

(75) Inventor: David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/395,512

(22) Filed: Sep. 14, 1999

(51) Int. Cl.[7] ........................................ A61B 5/04
(52) U.S. Cl. ..................... 600/545; 128/901; 128/902; 128/908
(58) Field of Search ..................... 600/372, 383, 600/545, 546, 547, 554, 301, 300, 509; 607/116, 63; 128/901, 902, 908

(56) References Cited

U.S. PATENT DOCUMENTS

| | | |
|---|---|---|
| 3,664,329 | 5/1972 | Naylor . |
| 3,830,226 | 8/1974 | Staub et al. . |
| 4,817,628 * | 4/1989 | Zealear et al. ............... 128/741 |
| 4,892,105 | 1/1990 | Prass . |
| 4,934,378 * | 6/1990 | Perry, Jr. ...................... 128/733 |
| 4,962,766 | 10/1990 | Herzon . |
| 5,161,533 | 11/1992 | Prass et al. . |
| 5,284,154 * | 2/1994 | Raymond et al. ............. 128/741 |
| 5,775,331 * | 7/1998 | Raymond et al. ............. 128/741 |
| 6,181,961 * | 1/2001 | Prass ............................. 600/547 |

OTHER PUBLICATIONS

Schwartz, Daniel M. and Rosenberg, Seth I.—"Facial Nerve Monitoring During Parotidectomy", Neuromonotinotirn in Otology and Head and Neck Surgery, Chapter 6, pp. 121–130 edited by J. Kartush and K. Bouchard, Raven Press, Ltd., NY 1992.

* cited by examiner

Primary Examiner—Jeffrey R. Jastrzab
Assistant Examiner—Frances P. Oropeza

(57) ABSTRACT

An economically manufactured, highly sensitive, noise and interference resistant, AC powered, two, four or eight channel intraoperative neuroelectrophysiological monitor includes a mainframe having a touch panel display and a low noise interface cable providing connection via a patient interface box for one or more stimulator probes and one or more EMG signal sensing electrodes.

6 Claims, 11 Drawing Sheets

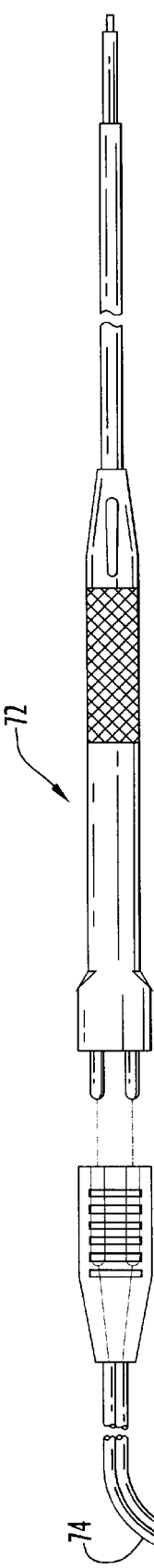
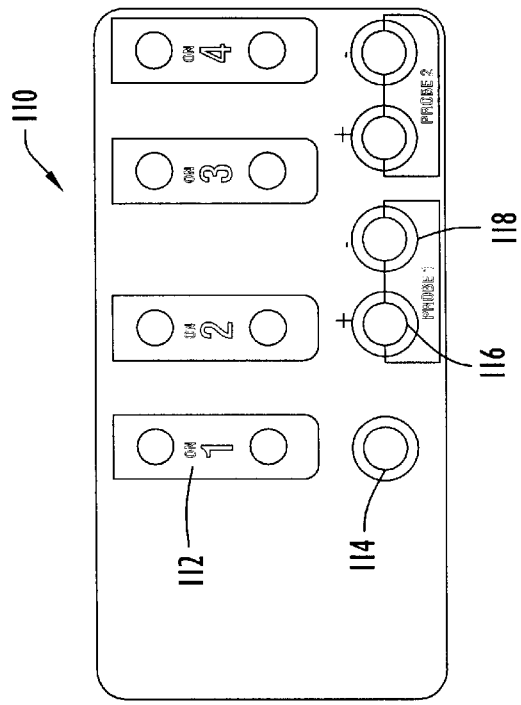
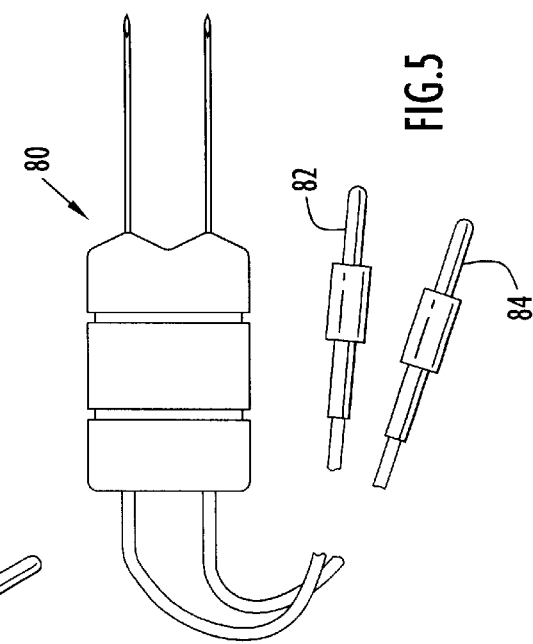
FIG.4
FIG.5
FIG.6

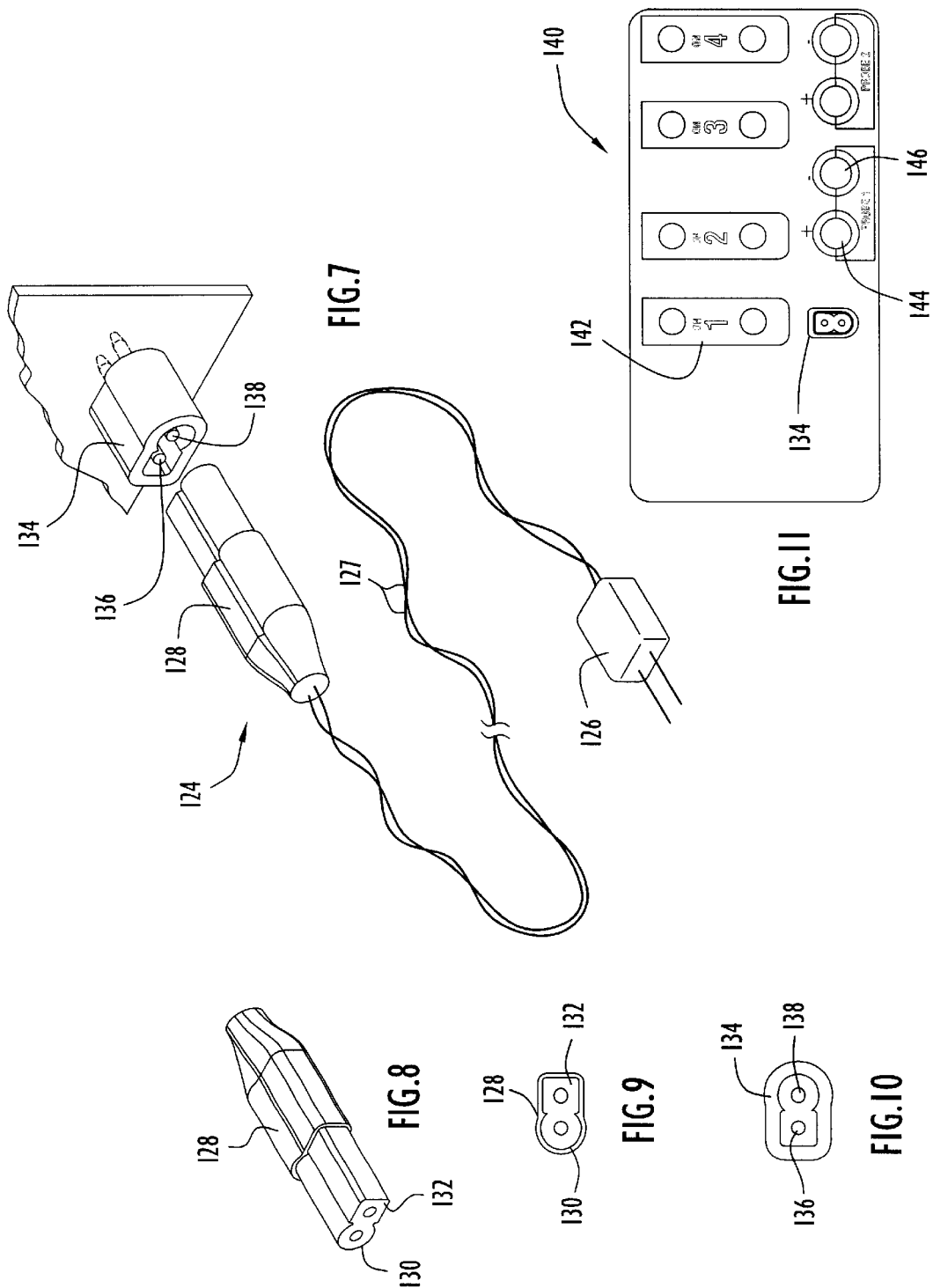

INTRAOPERATIVE NEUROELECTROPHYSIOLOGICAL MONITOR

BACKGROUND OF THE INVENTION

1. Field of the Invention

The present invention relates to surgical apparatus and more particularly to a neuroelectrophysiological monitoring instrument for use in conjunction with one or more electrical stimulus probes as an intraoperative aid in defining the course of neural structures. The invention is particularly applicable for use in monitoring facial electromyogram (EMG) activity during surgeries in which a facial motor nerve is at risk due to unintentional manipulation and will be described with reference thereto, although it will be appreciated that the invention has broader applications and can be used in other neuroelectrophysiological monitoring procedures.

2. Discussion of the Prior Art

Despite advances in diagnosis, microsurgical techniques, and neurotological techniques enabling more positive anatomical identification of facial nerves, loss of facial nerve function following head and neck surgery such as acoustic neuroma resection remains a significant risk. Nerves are very delicate and even the best and most experienced surgeons, using the most sophisticated equipment known, encounter a considerable hazard that a nerve will be bruised, stretched or severed during an operation. Studies have shown that preservation of the facial nerve during acoustic neuroma resection may be enhanced by the use of intraoperative electrical stimulation to assist in locating nerves. Very broadly stated, the locating procedure, also known as nerve integrity monitoring, involves inserting sensing or recording electrodes directly within cranial muscles innervated or controlled by the nerve of interest. A suitable monitoring electrode is disclosed in U.S. Pat. No. 5,161,533 (to Richard L. Prass et al.), the entire disclosure of which is incorporated herein by reference.

Electrical stimulation is then applied near the area where the subject nerve is believed to be located. If the stimulation probe contacts or is reasonably near the nerve, the stimulation signal applied to the nerve is transmitted through the nerve to excite the related muscle. Excitement of the muscle causes an electrical impulse to be generated within the muscle; the impulse is transferred to the recording electrodes, thereby providing an indication to the surgeon as to the location of the nerve. Stimulation is accomplished using hand held probes such as the Electrical Stimulus Probe disclosed in U.S. Pat. No. 4,892,105 (to Richard L. Prass), the entire disclosure of which is incorporated herein by reference. The probe of Pat. No. 4,892,105 has become known as the Prass Flush-Tip Monopolar Probe and is insulated up to the distal tip to minimize current shunting through undesired paths. An improved structure for a bipolar probe is disclosed in patent application Ser. No. 09/362,891 entitled Bipolar Electrical Stimulus Probe, the entire disclosure of which is also incorporated herein by reference.

Prior art nerve integrity monitoring instruments (such as the Xomed® NIM-2® XL Nerve Integrity Monitor, manufactured by the assignee of the present invention) have proven to be effective in performing basic functions associated with nerve integrity monitoring such as recording EMG activity from muscles innervated by an affected nerve and alerting a surgeon when the affected nerve is activated by application of a stimulus signal, but are not suitable for some surgical applications and present difficulties in certain environments.

The Xomed® NIM-2® XL Nerve Integrity Monitor (or NIM-2XL monitor) is powered by specially adapted battery packs for low noise operation. The 110 Volt Alternating Current (AC) mains supply is a well known source of 60 Hz him, RF interference and voltage spikes, and so the designers of the NIM-2XL monitor opted to avoid introduction of any possible interference in the highly sensitive low noise amplifiers required to sense microvolt ($\mu$V) level nerve monitoring signals by relying on battery power. In day-to-day practice, however, the battery packs are not always sufficiently charged to operate the NIM-2XL monitor for the required length of time; alternatively, the user may not have a sufficient quantity of fully charged battery packs for a lengthy procedure, since the staff may forget to recharge depleted battery packs. In response to these difficulties, users have asked for a nerve integrity monitor that can be connected to the 110V AC mains supply; those users still require highly sensitive nerve integrity monitoring circuitry, however.

The NIM-2XL monitor provides two channels of EMG monitoring, a sufficient configuration for at least 90% of the head and neck procedures performed, at present. It is anticipated that in the future, however, four or more channels of monitoring might be required for perhaps one in three head and neck procedures. This presents an economic difficulty since the NIM-2XL monitor is an expensive instrument and very few medical facilities could muster two or more NIM-2XL monitors (with fully charged battery packs) in response to this anticipated need.

Another problem arises in foreign countries which often lack surgical staff trained in the English language. The NIM-2XL monitor includes user screens with extensive directions for electrode placement and the like, all written in English, and so is not particularly well suited to use in non-English speaking environments.

Users have also requested improved EMG monitoring sensitivity. At present, the NIM-2XL monitor provides the ability to distinguish EMG events having an amplitude of approximately 25 $\mu$V; it would be desirable to provide sensitivity and noise rejection allowing one to distinguish events having an amplitude of 10 to 15 $\mu$V. Highly sensitive signal amplifiers are difficult to isolate from 60 Hz hum, RF noise and interference, however, and, as noted above, are often not compatible with power supplies connected to a noisy 110V AC mains supply. If additional sensitivity and noise rejection were provided however, the users would be able to detect smaller myogenic events than is currently possible.

Users have also noted that monitoring of probe continuity presents another set of problems. Periodic checks for probe continuity do not provide timely alerts to the surgeon or OR staff, in the event that probe continuity is interrupted during a procedure.

Users have noticed that certain kinds of artifacts have a disruptive effect on monitoring and tend to cause undesirable false alarms. In particular, EMG monitoring often is performed with electrocautery in a surgical procedure, wherein powerful currents surge through and cauterize the tissue, often to devastating effect on the monitor's sensitive amplifier circuits; electrocautery can also induce an undesired DC offset from buildup of charge on the monitoring or sensing electrodes. Additionally, pop noise (in the form high frequency spikes) is observed when non-insulated instruments are accidentally brought into contact, thereby providing threshold triggering false alarm. Often. false alarms are attributable to changes in what may be deemed background noise, which may be falsely identified as genuine EMG signals. Monitoring time is reduced by undesired and distracting false alarms, and so any solution to false alarms would increase the accuracy and effectiveness of the monitoring procedure.

Often, other sensitive electronic instruments are in use when intraoperatively monitoring neuroelectrophysiological signals in the body and these other instruments are also likely to be disrupted by electrocautery or the like. It may not be possible to clamp multiple muting detector sensors near the electrocautery instrument, and so clutter becomes a problem when performing delicate surgery in the head or neck.

Others have noted the problem in detecting true EMG signals even when muting and other sources of interference don't present a problem. In particular, authors Daniel M. Schwartz and Seth I. Rosenberg identified spurious activity when sensing a recording channel and dubbed it "artifact contamination" from the "antenna effect" created by placement of numerous hemostats in the operative field. Additional electrodes including a "control" electrode were described for use in method to improve spatial selectivity while discriminating between true EMG and the undesired "artifacts". Schwartz and Rosenberg's description of facial nerve monitoring is included as Chapter 6, pages 121 through 130, of the text *Neuromonitoring in Otology and Flead and Neck Surgery*, edited by J. Kartush and K. Bouchard, Raven Press, Ltd., 1992, the entirety which is incorporated herein by reference. Schwartz and Rosenberg have identified one method to discriminate spurious artifact signals from desired EMG signals in the innervated muscle using a signal provided by the control electrode spaced far away from the EMG electrode. In brief, if activity in the control channel is present, then it is deemed to be a product of artifact contamination.

A problem associated with using Schwartz and Rosenberg's suggested method is that monitoring instruments of the prior art customarily include two or fewer channels and so the controlled channel must somehow be configured to use a channel ordinarily reserved for an EMG sensing electrode. This problem confounds the above mentioned difficulties with properly placing electrodes and maintaining the electrical continuity of electrodes in the body. If an electrode falls out or if an electrode is misidentified as being either the control electrode or the innervated muscle EMG electrode, then that confusion may lead to an error during the procedure.

Turning to another concern, nerve integrity monitors of the prior art require the user to perform periodic checks before use, to make sure that the monitor is operating properly; as an example, an electrode imbalance check must be performed periodically to make sure that electrode placement is proper when imbalance is greater than, e.g., 20% of the greatest electrode impedance. Each check takes valuable time. The surgical staff does not have time to spare, since operating room time is exceedingly expensive and the user often has to set the monitoring instrument up in a selected configuration for a specific procedure, before beginning surgery.

There is a need, then, for a nerve integrity monitoring instrument having greater flexibility in use, greater sensitivity and noise rejection, enhanced ability to help resolve differences between genuine EMG signals and background noise and, as always, the lowest possible manufacturing cost.

OBJECTS AND SUMMARY OF THE INVENTION

Accordingly, a primary object of the present invention is overcoming the above mentioned difficulties by providing an improved method and apparatus for sensing electrical activity in nerve tissue.

Another object of the present invention is economically manufacturing an intraoperative neuroelectrophysiological monitor having four (or more) channels with improved monitoring sensitivity, despite use of economical AC mains supply power sources.

Another object of the present invention is improving spurious artifact rejection and noise rejection.

Yet another object of the present invention is overcoming the clutter problem associated with requiring use of multiple muting detector clamps when using multiple sensitive electronic instruments.

The aforesaid objects are achieved individually and in combination, and it is not intended that the present invention be construed as requiring two or more of the objects to be combined unless expressly required by the claims attached hereto.

In accordance with the present invention, an economically manufactured, highly sensitive, noise and interference resistant, AC powered, two, four or eight channel intraoperative neuroelectrophysiological monitor includes a mainframe having a touch panel display and a connection to a low noise interface cable providing a connection via a patient interface box for connecting one or more stimulator probes and one or more EMG signal sensing electrodes.

Monopolar or bipolar stimulator probes are used to apply a stimulus signal during surgery for nerve integrity monitoring or the like. The EMG electrodes are inserted into the body and sense electrical EMG signal energy within the body for monitoring and recording EMG activity within muscles innervated by an affected nerve being monitored.

The intraoperative neuroelectrophysiological monitor main frame includes an electrophysiological response signal processing circuit or patient interface control circuit having, preferably, four or more isolated instrumentation amplifiers and associated electrode impedance checking circuitry. The electrophysiological response signal processing circuit provides an output signal to an audio mixer or multiplexer circuit for generating audio alarms. The audio mixer is connected to a loudspeaker driving amplifier.

The intraoperative neuroelectrophysiological monitor mainframe also includes a muting detector circuit connecting to a muting detector probe adapted for use with electrocautery instruments or other instruments having a propensity for generating significant currents or voltages in the body during the nerve integrity monitoring procedure. The muting detector circuit provides a second input to the audio mixer/multiplexer circuit so that an audible annunciation of muting is provided. The electrophysiological response signal processing circuit also provides an input to an analog to digital (A/D) and digital to analog (D/A) converter circuit which digitizes signals from the isolated instrument amps for input to a central processing unit (CPU). The CPU receives inputs from a touch panel interface and provides display output information to the touch panel display. Optionally, a floppy disk drive is included in the mainframe and connected to the CPU. The mainframe includes a power supply with a line cord permitting the nerve integrity monitor to be powered by 110/120 volt AC from a mains supply connection (e.g., an electrical outlet).

The intraoperative neuroelectrophysiological monitoring instrument of the present invention can be configured with one to nine channels for EMG monitoring. For a four channel configuration, the electrophysiological response signal processing circuit includes first, second, third and fourth isolated instrument amplifiers, preferably all configured on a single printed circuit board, channels for monitoring relatively low amplitude EMG electrode signals. The isolated instrument amplifier board includes isolation transformers, optical isolators, input amplifiers, overload protection circuitry and EMG lead impedance measurement circuitry for checking the condition and connections of the EMG input leads and, optionally, the stimulator output circuits. Each isolated amplifier board also includes a stimulator output and measurement circuit for providing the stimulator output signal to be applied to the monopolar or bipolar stimulator output probes via the patient interface.

Advantageously, each isolated instrument amplifier is configured to amplify both high frequency EMG signals which will, for purposes of nomenclature, be referred to as alternating current (AC) signals and low frequency baseline change signals which will, for purposes of nomenclature, be referred to as pseudo-direct current (DC) signals. The isolated instrument amplifiers or strip amplifiers perform four functions simultaneously, namely, amplifying AC EMG signals, amplifying and dividing out the DC baseline change signals, patient isolation, and signal magnitude limiting including clamping the input sensed voltage and limiting swing of the output signals. Each isolated instrument amplifier includes a plurality of gain and filtering stages including a first input protection stage, a second gain stage amplifying both AC and DC, a third stage with adjustable gain and filtering, a fourth stage providing isolation followed by two filtering stages.

The DC baseline signal, is used in a number of subsequent signal processing steps; the time varying DC offset is subtracted from the composite signal so that EMG signals are displayed without offset. If DC offset exceeds a given value, it is likely due to an EMG sensing electrode having fallen out of the patient, in response, an alarm is sounded and normal EMG audio is muted.

The intraoperative neuroelectrophysiological monitor of the present invention also includes a data acquisition and control circuit board receiving impedance measurement data, stimulator output signals and measurements and the EMG isolated input signals. The data acquisition and control board provides outputs to the audio mixer/multiplexer circuitry for up to eight channels. The audio mixer board provides both voice and tone or warble prompts which are played through the loud speaker amplifier connected to the externally directed loud speaker. The CPU is connected to the data acquisition and control board and receives data therefrom. The CPU is also connected to the electroluminescent display and the touch panel incorporated into the display. A front panel interface card provides a video driving signal to the display and receives the input signals from the touch panel sensor areas. The front panel interface card also includes a low power alarm circuit providing an enunciation to the user of low or insufficient power provided by the nerve integrity monitor power supply.

The CPU also receives an input from a muting detector and stimulation foot control circuit which receives an input from the stimulator foot control used by the surgeon to cue or begin generation and application of the nerve stimulation signal. The muting detector and stimulation foot control circuit also receive an input from a muting detector clamp when applied to electro-cautery or other instruments tending to provide interference and diminish the performance of or interfere with the operation of the nerve integrity monitor. The muting detector circuitry of the present invention is an improvement over that described in U.S. Pat. No. 4,934,377 (to Joseph A. Bova and Richard L. Prass), the entire disclosure of which is incorporated herein by reference. The improved muting detector of the present invention includes an input circuit receiving output from up to four detector clamp sensors and a foot switch used for deliberate muting by the surgeon. The input circuit rectifies, clamps and selectively amplifies the detector clamp sensor signals and generates a TTL logic output signal which is logically OR'ed with the foot switch signal, thereby generating a processed muting input signal received through an input port to the monitoring instrument CPU. The CPU is used to process the muting function and will generate a Mute Now signal in response to any one of the following conditions: external detector muting (actuation of the muting input signal), "lead off" muting (indicating detection of a sensing electrode which has fallen out of the body), input signal overload muting, or excessive DC offset muting. The CPU Mute Now signal is input to a final processing circuit providing isolation, buffering, and overload protection to generate a muting distribution signal; the output of the final processing circuit is preferably brought out to an electrical connector mounted on the mainframe housing.

Another feature of the present invention is the enhanced controlled channel input circuit and bipolar ground electrode with polarized plug which permits easy and error-free introduction of a controlled channel electrode in the body while simultaneously inserting the ground electrode. A bipolar ground electrode and polarized plug assembly include a two-pin color coded bipolar electrode which is readily distinguished from normal innervated muscle EMG sensing electrodes by surgical staff in the OR. A flexible wire connects the color coded bipolar ground electrode to a polarized ground connector plug having a keyed or bias connector housing enclosing first and second conductors. The first conductor is used in conjunction with the first pin in the bipolar ground electrode to perform the usual ground return function associated with nerve integrity monitoring and delivery of a stimulus signal to the body. The second pin of the color coded bipolar ground electrode and the second conductor within the polarized ground plug housing are used to conduct controlled channel signal to the monitoring channel of the instrument. In the preferred embodiment, a bipolar ground interface connection panel provides the polarized jack adapted to receive the polarized ground plug in only one possible orientation, thereby avoiding possible mix-ups as to which electrode needle is the control channel conductor and which electrode needle is the ground conductor. Preferably, the interface polarized jack is incorporated into the interface connection panel alongside a plurality of the EMG sensing electrode connectors, each of which use the traditional dual RCA or dual banana plug connectors, as are well known in the prior art.

AC power from the 110/120 V AC mains supply is conditioned in an isolated power supply and is filtered for electro-magnetic-interference (EMI). An AC printer power connection is taken directly from the AC input connection. The isolated power supply provides +12 volt, +5 volt, 18 volt AC and ground or AC common lines for distribution from a power supply regulation and connection board having a plurality of electrical connectors. The power supply regulation and connection board is used to distribute power throughout the interior of the nerve integrity monitor mainframe and provides external power connections for the interface, muting detector and the like. Each of the major components of the nerve integrity monitor receive power from the power supply regulation and connection board, including the CPU, A/D-D/A card, audio mixer/mux card, electroluminescent display, front panel interface card, isolated instrumentation amps, and the loudspeaker amp.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 4 is a perspective illustration of a bipolar stimulus probe for use with the intraoperative neuroelectrophysiological monitor of the present invention.

FIG. 5 is an illustration of an EMG sensing electrode for use with the intraoperative neuroelectrophysiological monitor of the present invention.

FIG. 6 is an illustration of the front panel of a patient interface connection box for use with the intraoperative neuroelectrophysiological monitor of the present invention.

FIG. 7 is a perspective illustration of the bipolar electrode and polarized dual ground plug assembly for use with the intraoperative neuroelectrophysiological monitor of the present invention.

FIG. 8 is a perspective illustration of the polarized dual ground plug of FIG. 7, for use with the intraoperative neuroelectrophysiological monitor of the present invention.

FIG. 9 is an end view, in elevation, of the polarized dual ground plug of FIGS. 7 and 8, for use with the intraoperative neuroelectrophysiological monitor of the present invention.

FIG. 10 is an end view, in elevation, of the patient interface socket adapted to receive the polarized dual ground plug of FIGS. 7, 8 and 9, for use with the intraoperative neuroelectrophysiological monitor of the present invention.

FIG. 11 is an illustration of the front panel of a patient interface connection box for use with the polarized connectors of FIGS. 7–10, as part of the intraoperative neuroelectrophysiological monitor of the present invention.

DESCRIPTION OF THE PREFERRED EMBODIMENT

Figure 1:
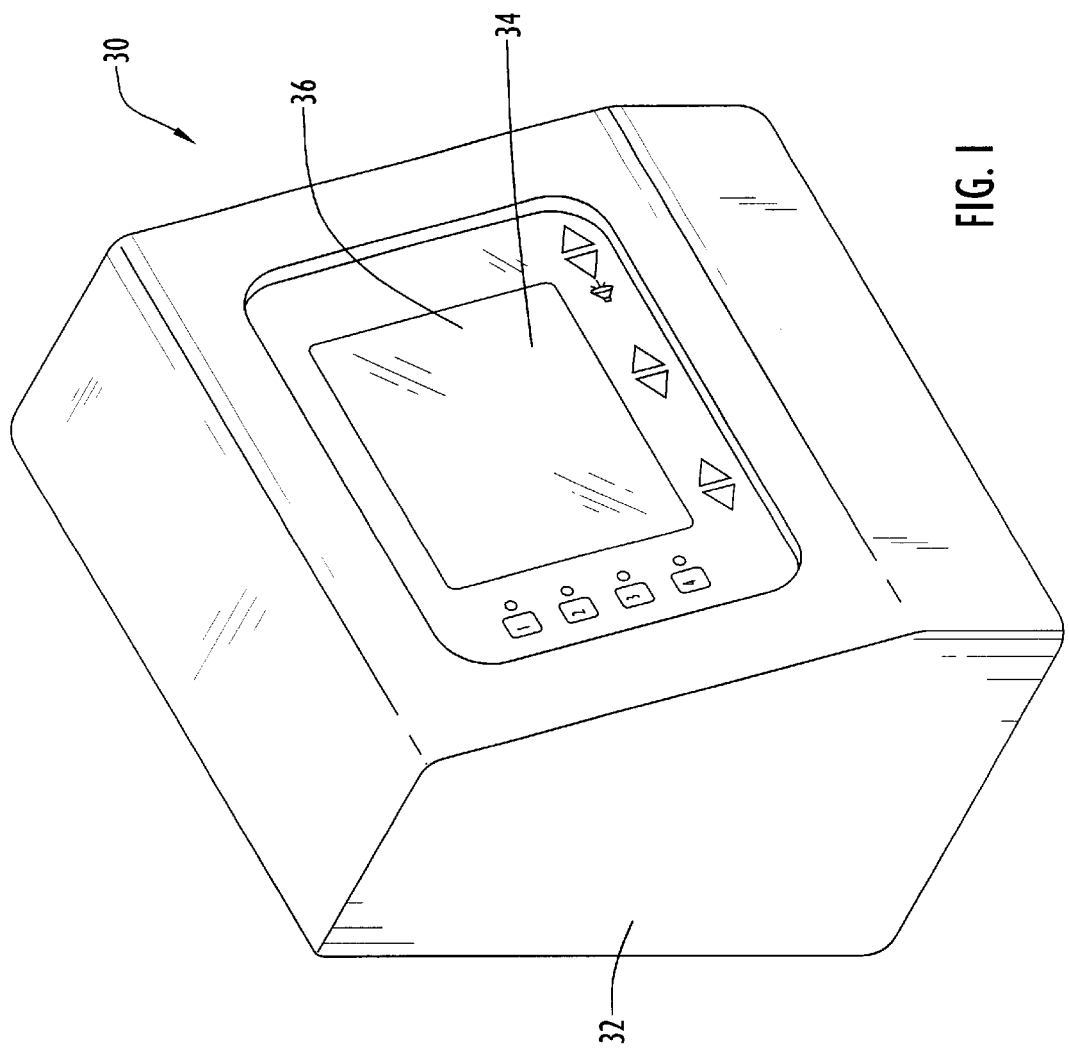
FIG. 1 is a perspective view of the intraoperative neuroelectrophysiological monitor main frame housing of the present invention.

Referring specifically to FIGS. 1–6, the neuroelectrophysiological monitoring instrument of the present invention includes a main frame 30 enclosed within a housing 32 having a display 34. The neuroelectrophysiological monitoring instrument of the present invention is used intraoperatively to pick up electromyographic (EMG) signals from the patient through subcutaneous electrodes 44 placed in the patient. The EMG electrode needles are placed below the surface of the patient's skin and the monitoring instrument is used intraoperatively in the operating room. The intraoperative neuroelectrophysiological monitor may also be used during injection of drugs (e.g., as when performing myography, as part of an outpatient procedure) and includes a stimulator section. An electrical stimulus delivered to a patient's nerve intraoperatively causes the nerve to be polarized; stimulus travels to the innervated muscle, causing the muscle to contract and providing small EMG voltages within the muscle that can be picked up by the EMG electrode needles placed in the muscles, thereby completing the circuit for the stimulus. The evoked response within the muscle is detected by the intraoperative neuroelectrophysiological monitor of the present invention as an EMG response signal; the monitor then generates an EMG audio signal of coded tones for annunciation over a speaker 50 positioned to be audible to a surgeon.

One or more electroluminescent displays 34 each include a touch panel or touch-screen 36 for accepting control inputs from the surgeon or user. The display touch panel 36 is preferably implemented as a resistive array.

Figure 2:
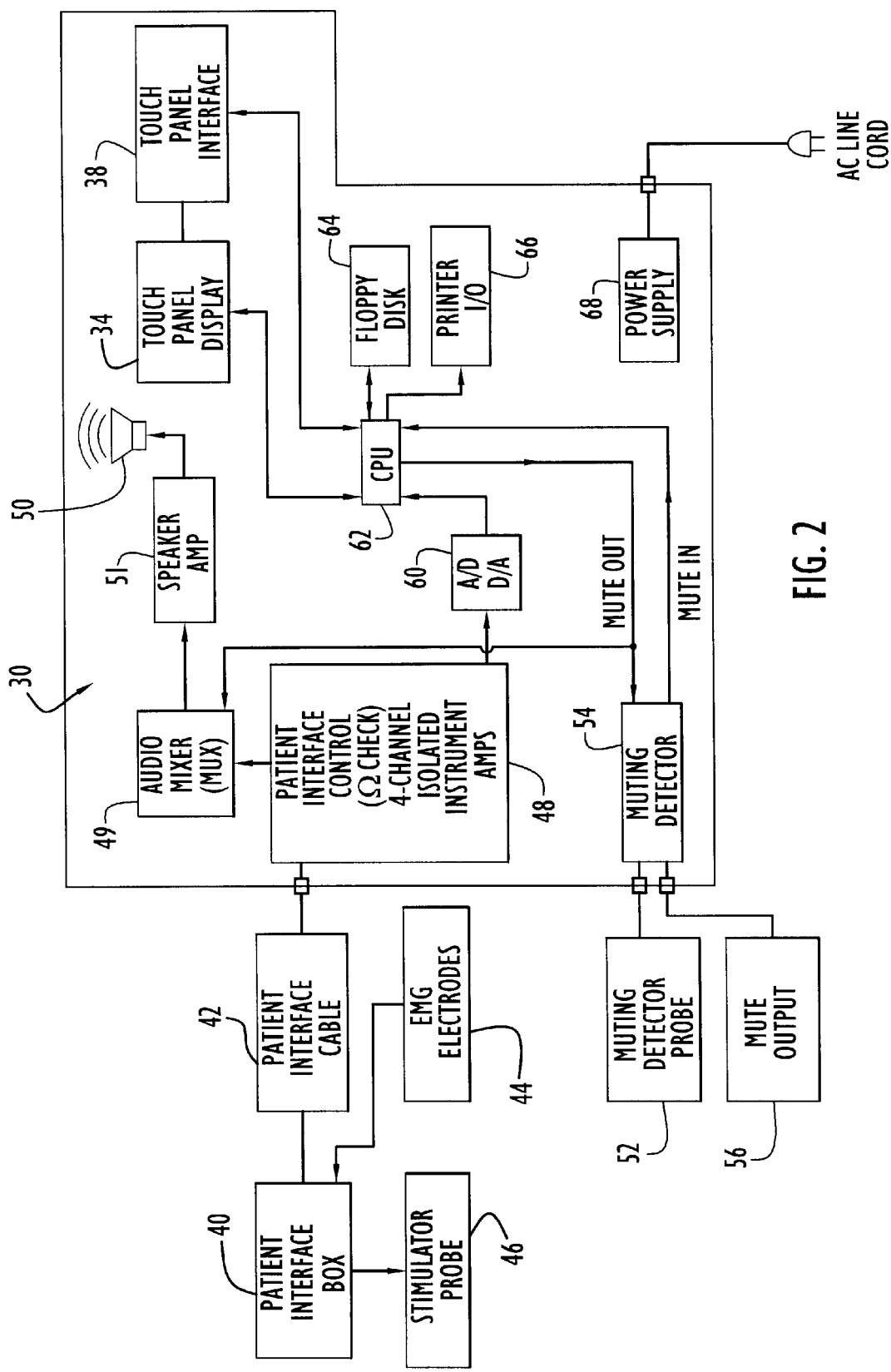
FIG. 2 is a block diagram illustrating the major components of the intraoperative neuroelectrophysiological monitor of the present invention.
Figure 3:
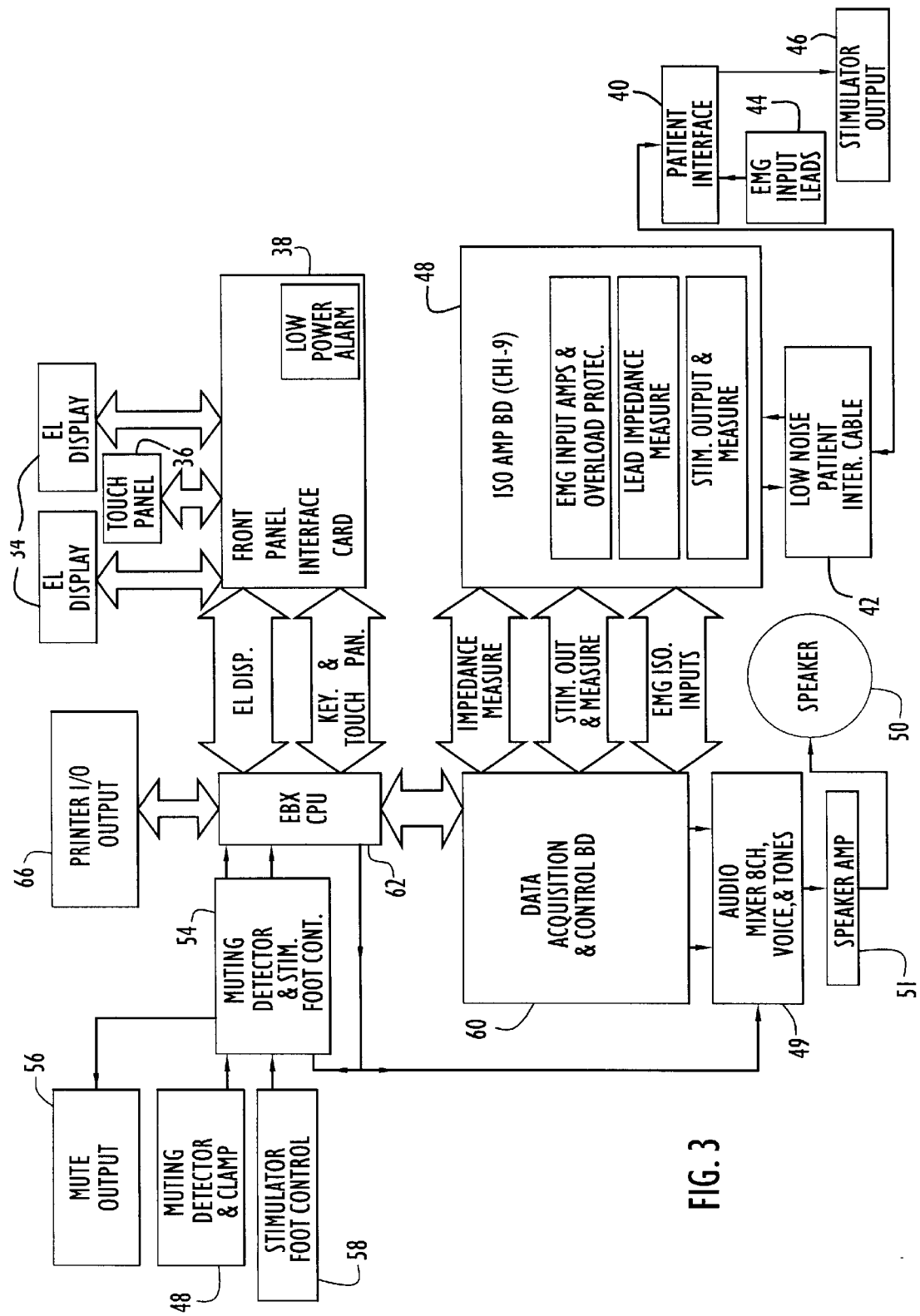
FIG. 3 is a block diagram illustrating signal flow between the major components of the intraoperative neuroelectrophysiological monitor of the present invention.

FIG. 2 is a block diagram illustrating the major components of the intraoperative neuroelectrophysiological monitor of the present invention; FIG. 3 is a block diagram illustrating signal flow between the major components. A patient interface 40 is connected via a low noise patient interface cable 42 to one or more EMG sensing input leads or electrodes 44 and one or more stimulator output (e.g., monopolar or bipolar) probes 46.

The patient interface connections through the low noise patient interface cable 42 are connected to the ISO amplifier board 48, with one to nine (preferably four) single channel amplifier circuits. The ISO amplifier board 48 is part of an electrophysiological response signal processing circuit including EMG input amplifiers with overload protection circuitry, lead impedance measurement circuitry, stimulator output circuitry and stimulator measurement circuitry. All inputs are isolated from the rest of the mainframe circuitry through transformer and optical coupling to provide up to 1000 volts RMS isolation from other connections to the mainframe, to protect and electrically isolate the patient. EMG signals enter the isolated instrumentation amplifier board through a 25 pin connector and pass through a diode protection network, thereby preventing damage to the instrumentation amplifier stages due to excess input voltage. The total amplification from the EMG inputs to the outputs is adjustable and preferably approximately 1:1200, a ratio expressed as magnitude of voltage input to magnitude of voltage output.

Figure 12:
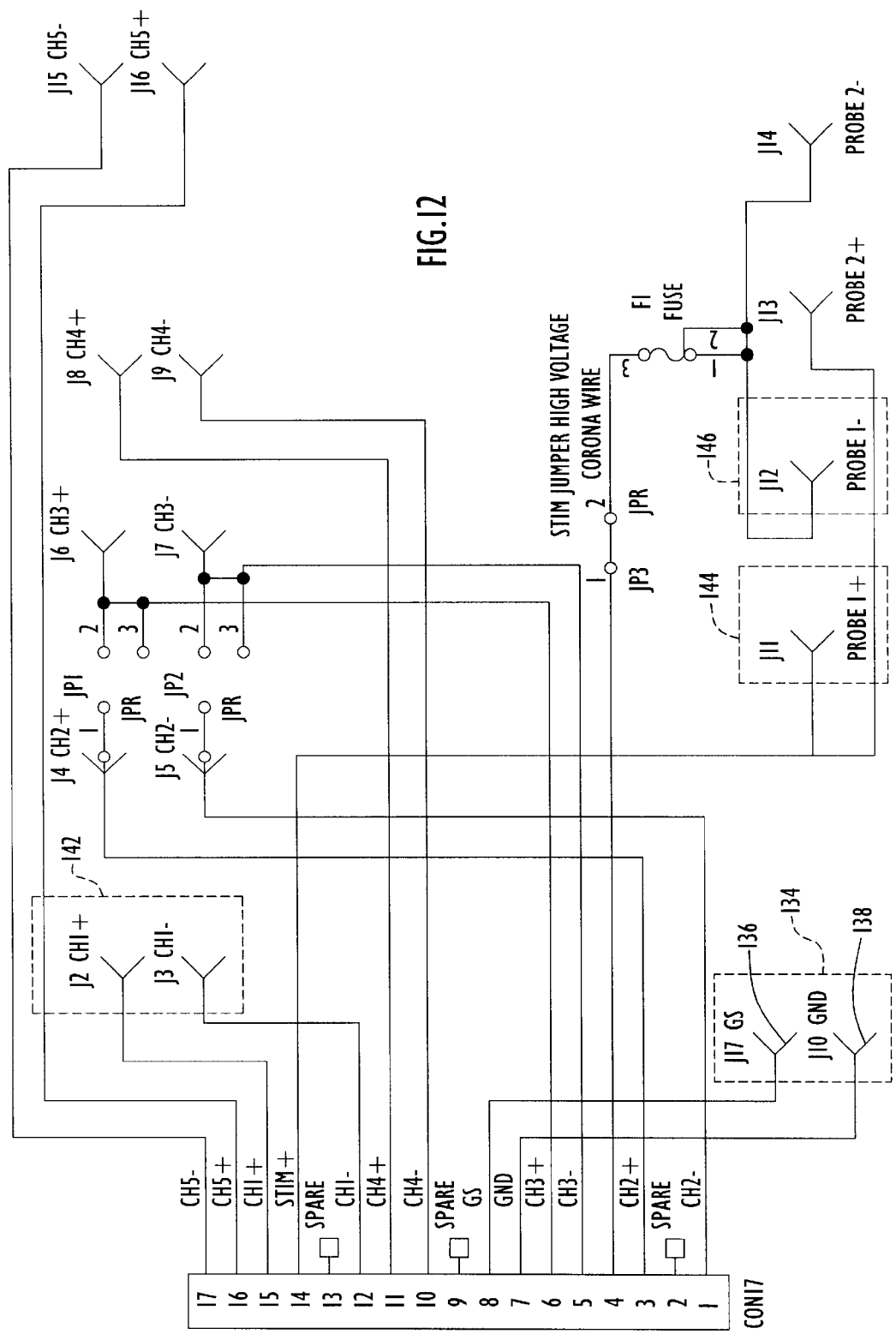
FIG. 12 is a schematic illustration of the electrical connections within the patient interface box of FIG. 11, for use with the intraoperative neuroelectrophysiological monitor of the present invention.

As will be discussed in greater detail below, there are two embodiments of the patient interface 40; the respective embodiments are illustrated in FIGS. 6, 11 and 12. FIG. 12 is an electrical schematic diagram illustrating the a preferred embodiment of patient interface control wiring.

Patient interface 40 is also preferably configured for four channels; optionally, the interface box provides connections for up to nine channels and is configured to provide shielded connections to the patient, either through one patient interface cable or through two patient interfaces connected to different connectors on the monitor main frame 30. As noted above, patient interface 40 is connected through special, low noise interface cable 42 which preferably includes one or more layers of electromagnetic shielding and provides optimized EMG signals to the instrumentation amps on the ISO amplifier board 48.

Turning to FIGS. 4, 5 and 6, FIG. 4 illustrates a bipolar electrical stimulus probe 72 connected by a flexible cable 74 terminated proximally in first and second pin connectors 76, 77. As best seen in FIG. 5, an EMG sensing electrode 80 includes first and second electrode pins terminated in distal conductive points, each of which is electrically connected with respective first and second EMG sensing electrical connectors 82, 84. The electrical stimulus probe, for delivering electrical stimulus to the body, and the EMG sensing electrode, for insertion in innervated muscles for sensing EMG in the body, are both connected to the monitoring instrument of the present invention through interface connection panel 110, as illustrated in FIG. 6. More particularly, the EMG sensing electrode connectors 82, 84 are placed in the receiving plugs in the panel using the EMG sense electrode connectors 112. A monopolar ground electrical connection from either a patch or a needle electrode is connected at ground electrical connector 114. A stimulus probe signal is output through probe connectors 116,118 which are adapted to receive bipolar probe connectors 76, 77 as shown in FIG. 4.

In the method of the present invention, between 1 and 9 of the sensing electrodes 80 are placed in different regions of interest in the body and are used to monitor between 1 and 9 separate EMG channels, one for each electrode. The stimulus probe (e.g., bipolar probe 72) is used to apply stimulus to the nerve structure of interest and the innervated muscles carrying the inserted EMG electrodes 80 are monitored to determine whether the integrity of the neural structure has been compromised during the course of the surgical procedure, for example.

Turning now to an alternative embodiment of the present invention, as illustrated in FIGS. 7, 8, 9,10 and 11, a bipolar ground electrode and polarized plug assembly 124 includes a color coded bipolar ground electrode 126 bearing first and second electrodes, each connected to a single flexible conductor of two wire flexible cable 127, to respective first and second conductors in the polarized ground plug 128. FIG. 8 illustrates the distal end of polarized ground plug 128 and shows the physical orientation of first connector 130 in the keyed or physically biased distal end; similarly, the differently shaped distal end proximate second connector 132 provides a structure which fits within a polarized socket or jack 134 included in the bipolar ground interface connection 140 of FIG. 11. The interface polarized jack 134 includes a first pin conductor 136 and second pin conductor 138 intended to engage the first and second female connectors 130, 132 within the distal end of polarized ground plug 128. Since polarized ground plug first connector 130 is included in a plug segment having a substantially circular cross section while the second conductor 132 of plug 128 is enclosed with a plug segment having a substantially square cross section, there is no way to mistakenly insert polarized ground plug 128 in the wrong orientation in interface jack 134, which is similarly polarized, since the respective receiving aperture segments of jack 134 are adapted to receive only the corresponding shapes of plug 128.

Bipolar ground interface connection panel 140 also includes the EMG sense electrode connector 142 for use with the sensing electrode 80 of FIG. 5 as well as plus and minus connectors for the bipolar stimulus probe 72, as with the embodiment of FIG. 4.

Alternatively, either of the interface panels disclosed above could be used with a monopolar stimulus probe such as, for example, the electrical stimulus probe disclosed in U.S. Pat. No. 4,892,105 (to Richard L. Prass).

FIG. 12 illustrates one embodiment of the electrical connections required to implement the bipolar ground interface connection panel 140 of FIG. 11. In particular, the interface polarized socket or jack 134 includes first pin conductor 136 and second pin conductor 138 designated as J17 and J10 in FIG. 12. The EMG sensing electrode input signal is provided in connector 142 identified as J2 and J3 in FIG. 12. Similarly, the output signal to the bipolar electrical stimulus probe plus and minus connections 144, 146 are identified as J11 and J12, respectively, in FIG. 12. All of the connections are brought through to a single electrical connector J1 for connection through the low noise interface cable described above.

In the method of the present invention, the bipolar ground electrode and polarized plug assembly 124 is used to provide an artifact sensing control channel positioned simultaneously with the customary ground return electrode. The extra monitoring channel provided by the color coded bipolar ground electrode 126 is placed in an electrically neutral area or muscle not innervated by the nerve being monitored. When an undesired artifact is present, it generally appears on all electrodes, including the disassociated color coded control electrode of the bipolar ground electrode 126, thereby indicating that an undesired artifact was sensed; conversely, when a sensed signal appears only on the monitored EMG electrode innervated by the desired muscle, and not on the control electrode 126, it is deemed a desired EMG signal. In this way, spurious or undesired artifacts are rejected and discriminated from EMG signals without requiring extra setup of a full extra monitoring channel and without requiring an extra channel electrode to be placed in the patient's skin during preparation for surgery in the OR.

The enhanced artifact rejection method of the present invention uses the bipolar electrode 126 placed in conjunction with the ground electrode and becoming, in essence, the control channel neutral area electrode. The color coded bipolar ground electrode 126 is used in conjunction with the ground electrode that is normally required when using neurophysiological monitoring equipment and, using the method of present invention, simplifies operating room practice. The ground sense electrode is also placed in an electrically neutral area or muscle not innervated by the nerve being monitored. In the method of the present invention, the user plugs the polarized plug 128 into the interface polarized socket or jack 134 in the only manner permitted by the structure of the plug socket, thereby avoiding confusion between the ground channel, monitored channels and the control channel. Alternatively, a bipolar plug assembly could be structured using a single wire ground to be plugged into the ground sense plug or receptacle for monitoring without a control channel being used.

Figure 15:
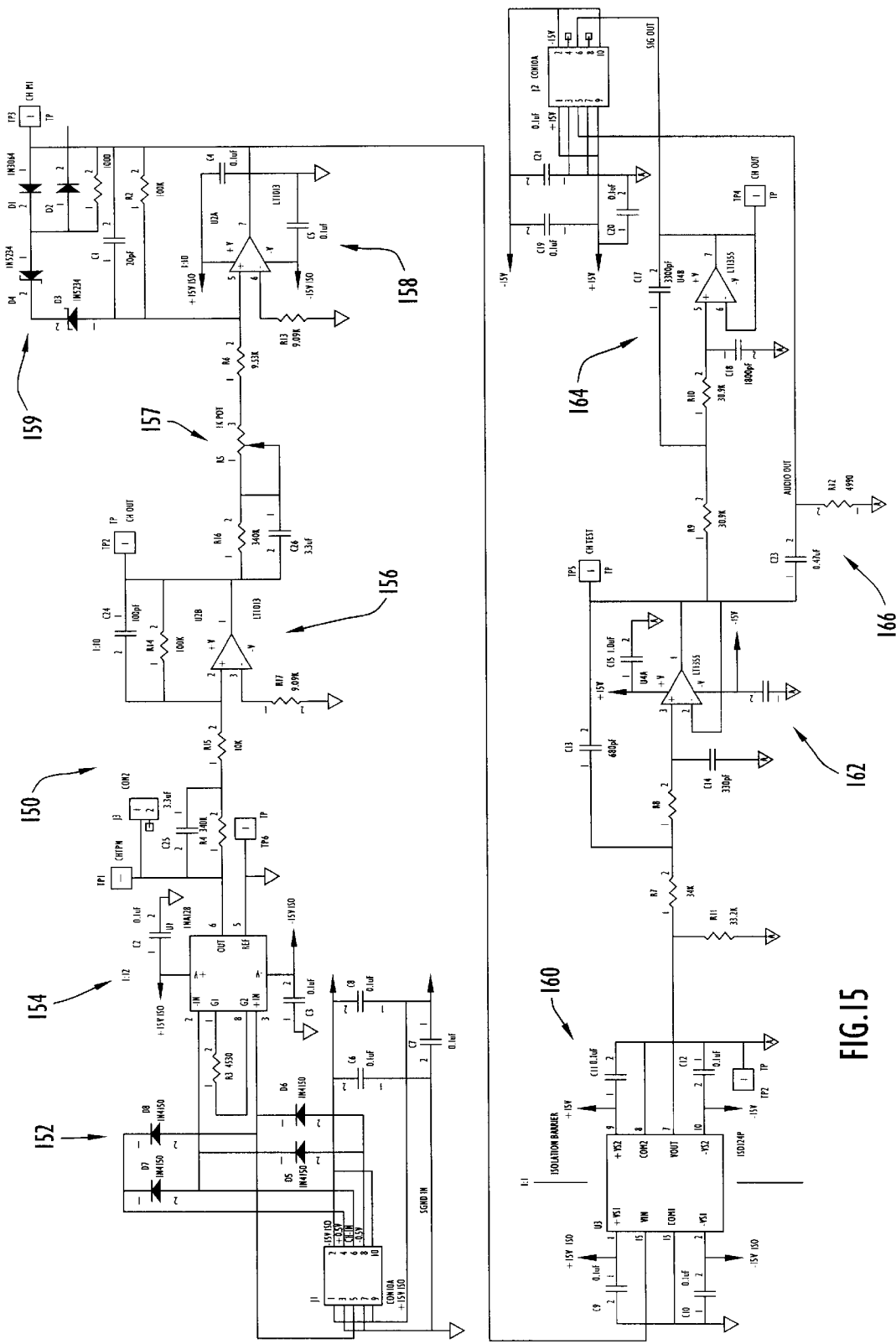
FIG. 15 is a schematic diagram of the single channel of AC/DC amplification shown in the block diagram of FIG. 13, for use with the intraoperative neuroelectrophysiological monitor of the present invention.

FIG. 15 is an electrical schematic diagram illustrating the circuitry of an isolated instrumentation amplifier 150, as incorporated into ISO amplifier board 48. Signal flow through the isolated instrumentation amplifiers is diagramatically illustrated in FIG. 13.

During the course of developing the intraoperative neuroelectrophysiological monitor of the present invention, it was determined that an electrophysiological response signal processing circuit was required having specific characteristics so that a low noise EMG monitoring instrument is implemented with inexpensive circuits having relatively low parts counts. One problem identified during the development effort was that conventional EMG instrument amplifiers required AC coupling, as by use of a series capacitor, in order to eliminate the DC offset provided by half-cell potential in the body. Often, the half-cell potential was observed to have much greater magnitude than the AC EMG signal superimposed thereon. By AC coupling the EMG signal processing amplifiers, it was possible to avoid overloading the amplifiers, since EMG signals tend to be in the order of millivolts while the large DC offset produced by the physiological phenomena of half-cell potential tended to be in the order of volts, a level very likely to produce overload in one or more stages of the isolated amplifier circuitry. Since it was determined that the DC or low frequency information was desirable to provide extra monitoring information, as described below, an additional electrically isolated connection would be required between the patient and the monitoring instrument when using AC coupled amplifier circuits. As noted above, there must be substantial electrical isolation between the patient and any electrical instrument, in the interest of protecting the patient from electric shock or the like. An additional connector and added isolation circuitry would make separate AC and DC signal processing circuitry excessively expensive, because of the higher parts count.

The EMG signal processing circuit of the present invention combines both rapidly varying AC and slowly varying DC electrophysiological response signals in one electrophysiological response signal processing circuit by implementing an isolation amplifier circuit including a plurality of gain stages adapted to amplify both the rapidly varying AC and slowly varying DC electrophysiological response signals. One of the problems confronted in this approach was selecting the gain and frequency response characteristics for each stage in the isolation of the prior circuit so that adequate sensitivity would be provided while avoiding problems associated with overloading the sensitive amplifier circuits. In particular, the AC amplification is greater than one thousand for the isolation amplifier circuit while the DC amplification is 1:1. Since the DC offset half-cell potential signal requires much less amplification.

Figure 13:
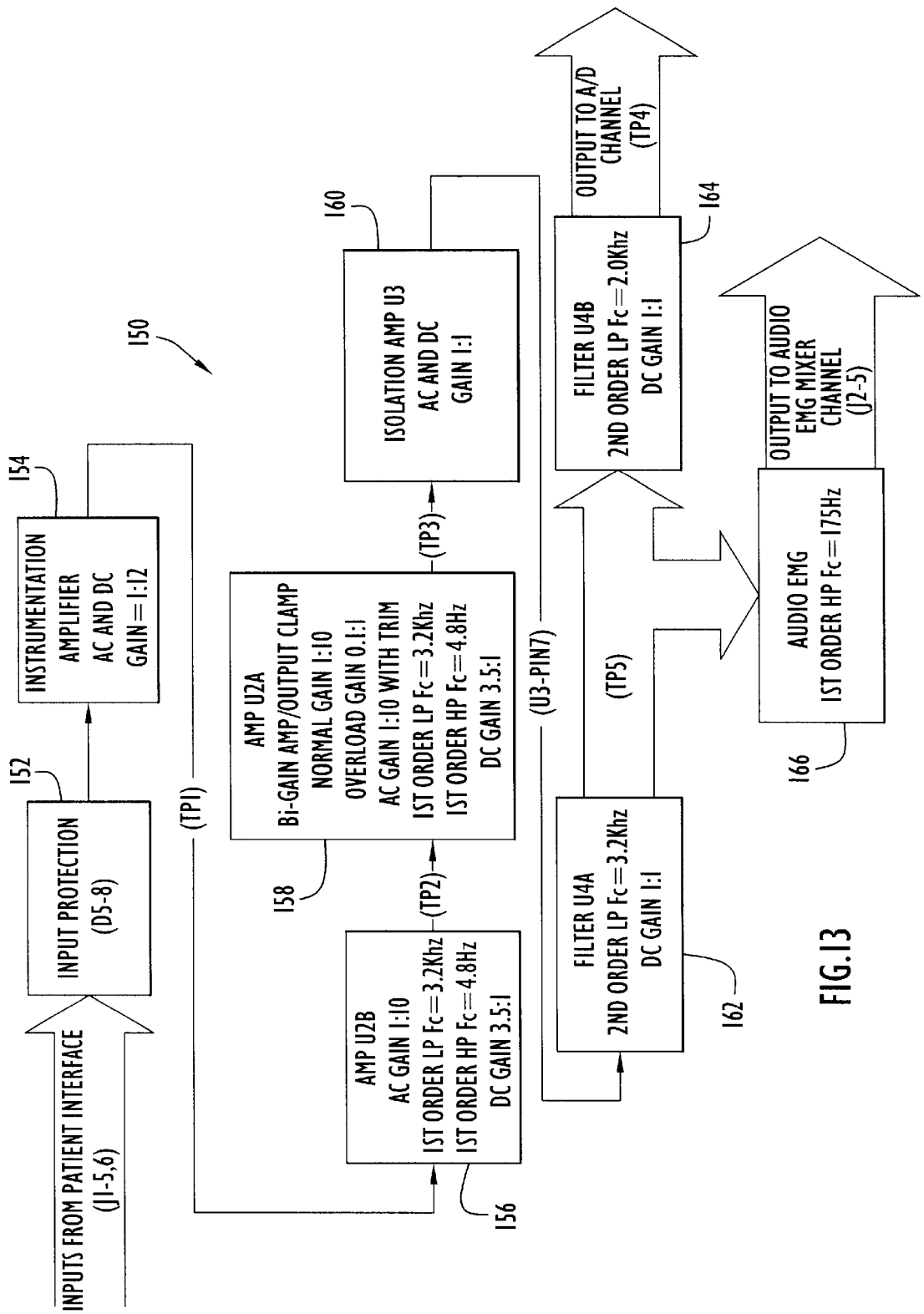
FIG. 13 is a signal flow block diagram of a single channel of AC/DC amplification, for use with the intraoperative neuroelectrophysiological monitor of the present invention.

Referring simultaneously to FIGS. 13 and 15, the first amplification stage 154 is identified as the instrumentation amplifier and provides AC and DC gain of 1:12, the second amplification stage 156 provides AC gain of 1:10 and has a first order low-pass filter cut-off frequency of 3.2 Khz and a first order high-pass cut-off frequency of 4.8 Hz; the DC gain for stage 156 is actually an attenuation of 3.5:1.

The next gain stage 158 is the bilinear or bi-gain amplifier output clamp stage having a normal gain of 1:10 and an overload gain of 1:0.1; the AC gain is adjusted to 1:10 with trimmer potentiometer 157 and stage 158 frequency characteristics are controlled by a filter switch with a first order low-pass cut-off frequency 3.2 KHz and a first order high-pass cut-off frequency of 4.8 Hz. Stage 158 has a DC gain or attenuation of 3.5:1.

The next gain stage 160 has both AC and DC gain set at 1:1, provides isolation and provides its output to succeeding filter stage 162 having a second order low-pass cut-off frequency of 3.2 KHz and a DC gain of 1:1. The output of filter stage 162 can be sampled at test point 5 and provides an input to the audio EMG stage 166 which has a first order high-pass cut-off frequency of 175 Hz and provides an output to the audio EMG mixer. The output of filter stage 162 is also and input to filter stage 164 having a second order (6 dB/octave) low-pass cut-off frequency at 2.0 KHz and a DC gain of 1:1. This combination of gain and filtering stages provides the appropriate amount of amplification for the rapidly changing or AC EMG signals while preserving the information contained in the slowly varying or DC offset signal.

The EMG signals enter the four-channel isolated instrumentation amp 48 through a 25 pin connector (e.g., a DB-25 connector) and the signal is input into a diode protection network 152, which prevents an instrumentation amplifier stage 154 from being damaged by excessive voltages. The total amplification from the EMG inputs to the outputs of the board (48) is adjustable to be approximately 1:1,200; as noted above the adjustment is performed by selecting the proper impedance for trimmer 157, as shown in FIG. 15, to achieve the approximate global AC gain value of 1,200.

Third amplification stage 158 is, for purposes of nomenclature, defined as a bi-linear amplifier, having two different gains, depending on the amplitude of the incoming signal. The bilinear amplifier stage 158 serves three functions, first, as noted above, the stage provides two different gains (depending on the input signal amplitude); second, the stage also serves to limit the maximum swing of the output voltage to further protect downstream circuitry from overload. In combination with the trimmer or potentiometer 157, bilinear amplifier stage 158 normally provides a gain of approximately 1:10. Through the normal EMG range, the bilinear amplifier stage will maintain a gain of 1:10 and will be linear up to approximately 9 volts, either negative direction or positive, at which voltage the diodes in clamping network 159 will start to conduct.

Figure 14:
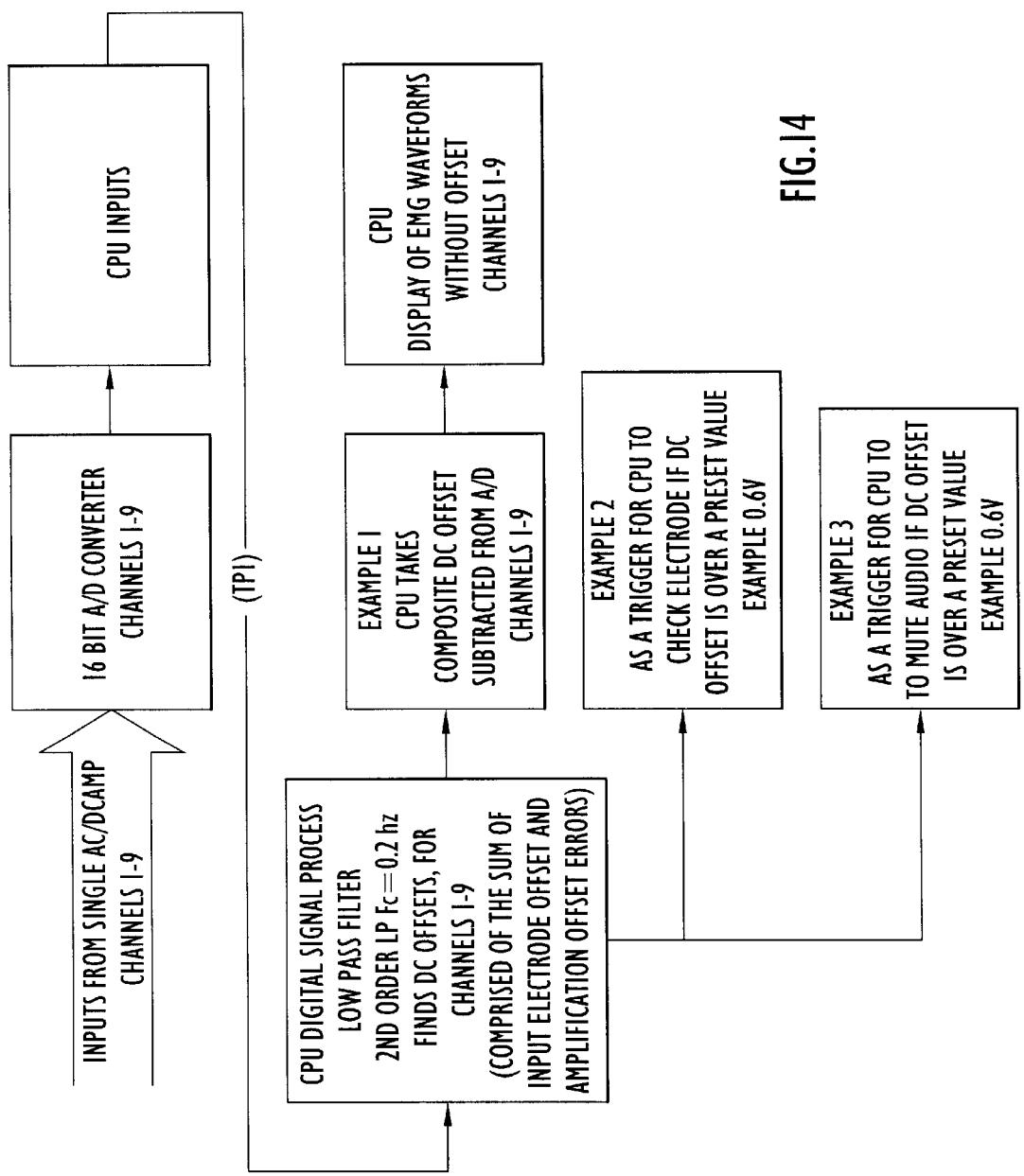
FIG. 14 is a signal flow block diagram of an electrophysiological response signal processing circuit receiving an input from the amplification channel of FIG. 13, for use with the intraoperative neuroelectrophysiological monitor of the present invention.

The diodes of clamping network 159, modify the gain of stage 158 to a new gain when the input signal level is in the range of 9 volts and approximately 9.6 volts, between which the gain will be approximately 1:0.6. If the incoming signal causes the voltage at the bilinear amplifier stage to exceed approximately 9.6V (either negative or positive), the voltage will be clamped from any further rise at about 9.7 volts; clamping is done by the IN 3064 diodes in clamping network 159, connected back to back. Additionally, each of the amplification stages, including the bilinear amplifier stage 158, has a simple RC active filter to attenuate high frequencies out of the range of interest. The bilinear amplifier stage's transfer function is the same for inputs in either the positive or negative direction, providing a gain of 1:10 for outputs up to 9 volts, for a further increase in the input signal generating an output of between 9 volts and 9.6 volts, the bilinear amplifier stage provides a gain of .6, and so output signal level further increases with increasing input signal level until the output signal reaches approximately 9.7 V, whereupon gain flattens and no further increase in input signal generates a corresponding increase the output of the bilinear amplifier stage. This would be reflected either for signals in the positive direction or in the negative direction. The EMG signals next cross an isolation boundary in stage 160 including an amplifier. The isolation boundary is preferably optically coupled. All the other circuitry with the exception of the stimulator circuit, is optically coupled. As shown in FIG. 14, EMG signals then are input to the A to D converter section 60. It should be noted that the multiplexing circuitry used for measuring the impedances multiplexors, in a special configuration allowing only one of the lines to be connected to each of the inputs to measure the impedances of the electrodes connected to the input of the unit. There is also a separate circuit for measuring the stim electrode, the measured voltages are returned to the A to D Converter and interpreted by solving simultaneous equations to figure out the impedance of all the leads. The input circuitry for each channel is duplicated for either two or four channels, or two boards for eight channels.

Returning now to the Block Diagram, FIG. 3, the data acquisition and control board has A to D converter section 60 including a sixteen channel A to D converter, two channels of D to A conversion, and sixteen channels of digital Input-Output (IO). A to D resolution is sixteen bits. The chain of amplification and the special biphasic or the bi-linear amplifier are carefully balanced to provide one quarter of one microvolt for each of the sixteen bit A to D resolution items, thereby providing the most dynamic range of all of the different parts along the chain.

The signals are then fed to the CPU, a 100 MHz 486 DX4 processor. The CPU board is interfaced with EL display(s) 34 and also with an (internal or external) keyboard. The internal keyboard is preferably on the face of the main frame housing 32, the optional external keyboard can be located separately and is preferably also connected to touch panel 36. The keyboard signals are processed through the front panel interface card 38 which includes a low power failure alert and is interfaced with the EL display(s). The front panel interface card 38 is additionally interfaced with the touch panel 36, and the keyboard and the keyboard lights.

The Audio Mixer 49 is a four channel mixer board which can also mix up to nine channels of EMG, the voices of the spoken words and tones. The audio mixer/mux 49 permits playback signal selection for any or all of these as well as volume or loudness control for playback through speaker 50. A phono-jack output (not shown) can also be independently controlled. The speaker amplifier provides a gain of 1:2 and is connected to high fidelity speaker 50.

The EMG signal thus goes into the input electrode leads 44, through the patient interface 40 and the low noise cable 42, into the instrumentation amplifiers, and then the audio EMG is split off separately, going directly into the audio mixer card 49 and not processed by the CPU, allowing for less processing overhead. The audio then goes through the mixer to the speaker amp 51 to the speaker 50, thereby completing the chain of the audio EMG as heard by the surgeon. The tones are generated by the CPU 62.

Figure 16:
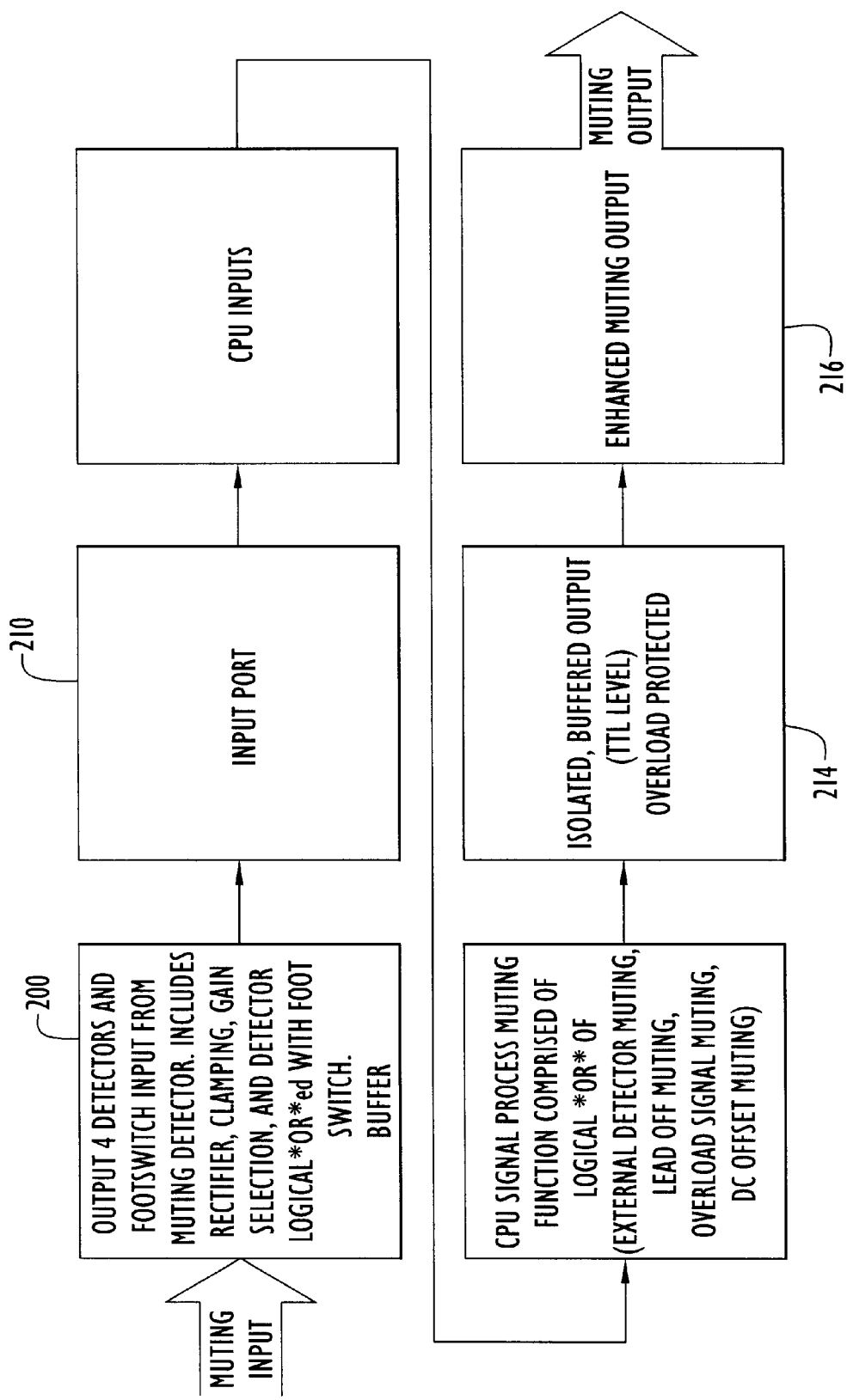
FIG. 16 is a signal flow block diagram of the improved muting detector circuitry, for use with the intraoperative neuroelectrophysiological monitor of the present invention.
Figure 17:
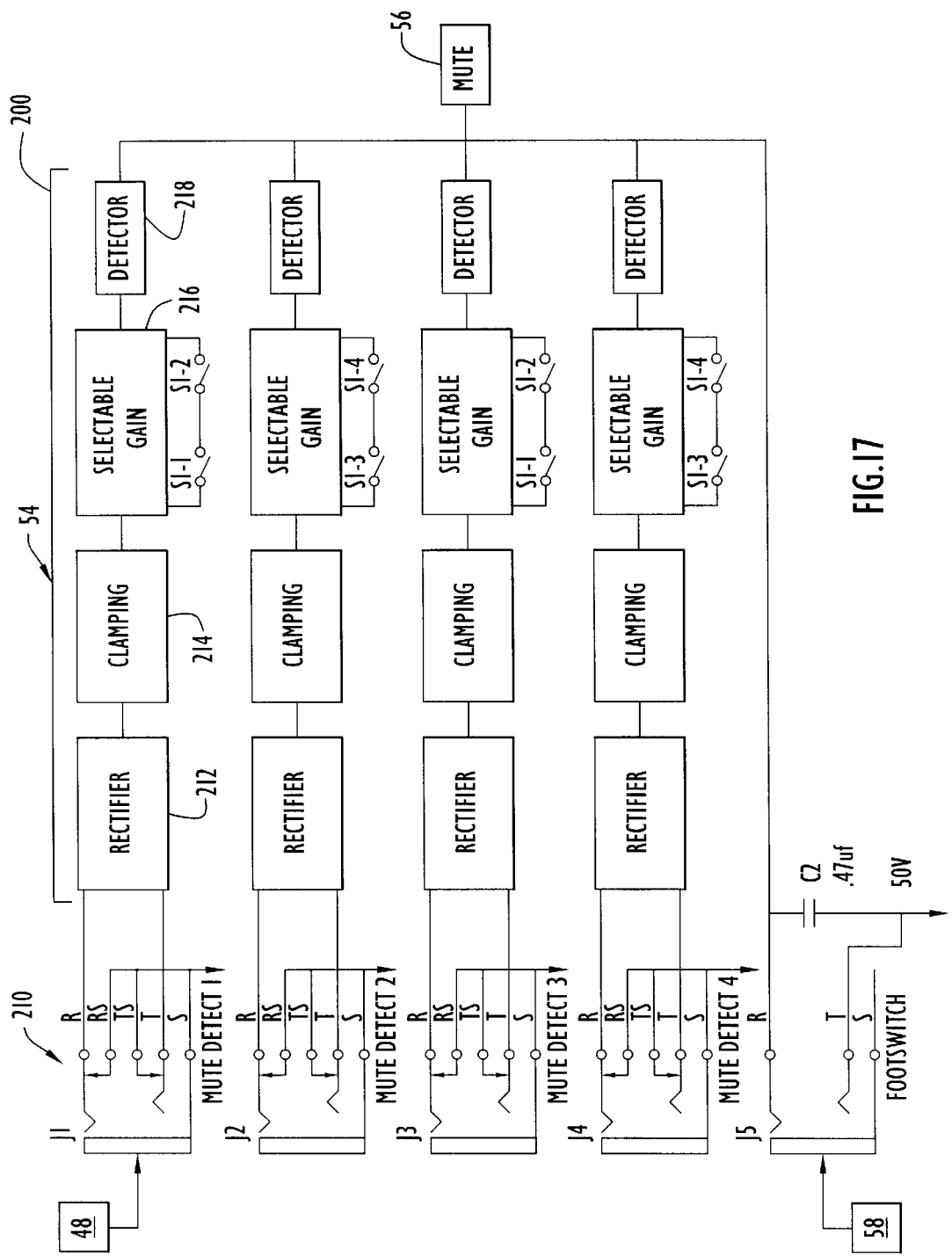
FIG. 17 is a schematic diagram of the improved muting detector, for use with the intraoperative neuroelectrophysiological monitor of the present invention.

Referring now to the left side and middle of FIG. 2, a muting detector clamp sensor or probe 52 provides input to the CPU, and also into the audio mixer 49 (either deliberately, on demand through operation of a footswitch, or through the use of an electrocautery device). A muting detector probe and circuitry automatically picks up RF activity and mutes the audio EMG to the surgeon. As best seen in the signal flow block diagram of FIG. 16 and the schematic of FIG. 17, the improved muting detector of the present invention includes an input circuit 200 which receives output from up to four detector clamp sensors (e.g., 48) and a foot switch used for on-demand muting by the surgeon. Input circuit 200 rectifies, clamps and selectively amplifies the detector clamp sensor signals and generates a TTL logic output which is logically OR'ed with the foot switch signal, thereby generating a processed muting input signal received through an input port 210 to the monitoring instrument CPU. The CPU is used to process the muting function and will generate a "Mute Now" signal in response to any one of the following conditions: external detector muting (actuation of the muting input signal), "lead off" muting (indicating detection of a sensing electrode which has fallen out of the body), overload signal muting, or DC offset muting. The CPU "Mute Now" signal is input to a final processing circuit 214 providing isolation, buffering, and overload protection to generate a muting distribution signal: the output of the final processing circuit is preferably brought out to an electrical connector 216 mounted on the mainframe housing.

Referring now to FIG. 2, the AC line in the lower right hand corner comes through a special filter block fused in an isolated power supply (medical grade) providing a level of isolation to all of the circuitry in the unit, in addition to the isolation provided by the instrumentation amplifiers.

Having described preferred embodiments of a new and improved method, it is believed that other modifications, variations and changes will be suggested to those skilled in the art in view of the teachings set forth herein. It is therefore to be understood that all such variations, modifications and changes are believed to fall within the scope of the attached claims defining the present invention.

What is claimed is:

1. An intraoperative neuroelectrophysiological monitor for use with an electrosurgery apparatus used in treatment of a surgical patient, for detecting or recording an electrophysiological response signal from the patient's body, said monitor comprising:

an electrophysiological response signal processing circuit responsive to the electrophysiological response signal, said electrophysiological response signal processing circuit generating an electrophysiological response enhanced monitoring signal;

said electrophysiological response signal processing circuit including an isolation amplifier circuit having an input and receiving the electrophysiological response signal at said input;

said isolation amplifier circuit including a gain stage adapted to amplify rapidly varying alternating current (AC) and slowly varying direct current (DC) electrophysiological response signals, wherein said gain stage has a first selected gain for rapidly varying (AC) signals and a second selected gain for slowly varying (DC) signals, said isolation amplifier circuit generating an amplified electrophysiological response signal having an (AC) component and a (DC) component; and said first gain being greater than said second gain.

2. The intraoperative neuroelectrophysiological monitor of claim 1, said electrophysiological response signal processing circuit further including a filter circuit with an input, said filter circuit being responsive to said amplified electrophysiological response signal and generating a filtered rapidly varying (AC) electrophysiological response signal and a filtered slowly varying (DC) electrophysiological response signal.

3. An intraoperative neuroelectrophysiological monitoring system used in treatment of a surgical patient, for detecting or recording biophysical responses resulting from electrical stimulation of the surgical patient from electrical stimulation signals, said monitoring system comprising:

a monitor mainframe having a housing;

an electrical stimulation signal generator within the monitor mainframe housing and having an output with an external electrical connection on the exterior of said housing;

an electrical stimulator probe connected to said electrical stimulation signal generator output, said stimulator probe having a conductive distal probe end adapted to conduct electrical stimulus to a selected site in the patient's body;

one or more monitoring electrodes adapted to conduct electrophysiological response signals from the patient's body;

an electrophysiological response signal processing circuit within the monitor mainframe housing and responsive to said monitoring electrode electrophysiological response signals, said electrophysiological response signal processing circuit generating an electrophysiological response display signal;

a bipolar ground electrode having a first ground electrode and a second control channel electrode for artifact detection.

4. An intraoperative neuroelectrophysiological monitoring system for use with an electrosurgery apparatus used in treatment of a surgical patient, for detecting or recording biophysical responses resulting from electrical stimulation of the surgical patient from electrical stimulation signals, said monitoring system comprising:

a monitor mainframe having a housing;

an electrical stimulation signal generator within the monitor mainframe housing and having an output with an external electrical connection on the exterior of said housing;

an electrical stimulator probe connected to said electrical stimulation signal generator output, said stimulator probe having a conductive distal probe end adapted to conduct electrical stimulus to a selected site in the patient's body;

one or more monitoring electrodes adapted to conduct electrophysiological response signals from the patient's body;

an electrophysiological response signal processing circuit within the monitor mainframe housing and responsive to said electrophysiological response signals, said electrophysiological response signal processing circuit generating an electrophysiological response display signal;

a clamp sensor pick-up within the monitor mainframe housing and connected to the electrosurgery apparatus, said pick-up responsive to activation of said electrosurgery apparatus and generating an electrosurgery apparatus activation signal;

a muting controller within the monitor mainframe housing and responsive to said pick-up electrosurgery apparatus activation signal, said muting controller generating a muting signal having a selected duration;

said electrophysiological response signal processing circuit also being responsive to said muting signal and disabling generation of said electrophysiological response display signal for a selected interval in response to detecting said muting signal;

a muting signal distribution circuit within said monitor mainframe housing and responsive to said muting signal for providing an external muting output signal; and a muting output connector on an exterior surface of the monitor mainframe housing and adapted to conduct said muting output signal.

5. The intraoperative neuroelectrophysiological monitor of claim 1, wherein said rapidly varying (AC) signals and said slowly varying (DC) signals have amplitudes, respectively, and said amplified electrophysiological response signal varies depending on said amplitudes.

6. The intraoperative neuroelectrophysiological monitor of claim 1, wherein said isolation amplifier circuit includes a bi-linear amplifier.

* * * * *